US00PP18726P3

(12) United States Plant Patent
Kaagman

(10) Patent No.: US PP18,726 P3
(45) Date of Patent: Apr. 8, 2008

(54) ***CAMPANULA* PLANT NAMED 'CAMP BULEWHIT '**

(50) Latin Name: ***Campanula isophylla* Moretti**
Varietal Denomination: Camp Bulewhit

(75) Inventor: Pim Kaagman, Andijk (NL)

(73) Assignee: Goldsmith Seeds Europe B. V., Andijk (NL)

( * ) Notice: Subject to any disclaimer, the term of this patent is extended or adjusted under 35 U.S.C. 154(b) by 100 days.

(21) Appl. No.: 11/412,518

(22) Filed: Apr. 27, 2006

(65) Prior Publication Data

US 2007/0256201 P1 Nov. 1, 2007

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

GTITM UPOVROM Citation for 'Camp Bulewhit 'as per QZ PBR 20050113; filed Jan. 24, 2005.*

* cited by examiner

*Primary Examiner*—Kent Bell
(74) *Attorney, Agent, or Firm*—Jondle & Associates, P.C.

(57) ABSTRACT

A new *campanula* plant particularly distinguished by large-sized blue and white, star-shaped flowers, an early and profuse flowering response, medium-green foliage with cordate leaves, moderately vigorous growth and a low, spreading and mounding, tight plant habit, is disclosed.

2 Drawing Sheets

Genus and species: *Campanula isophylla* Moretti.
Variety denomination: 'Camp Bulewhit'.

BACKGROUND OF THE NEW PLANT

The present invention comprises a new and distinct cultivar of *campanula,* botanically known as *Campanula isophylla* Moretti, and hereinafter referred to by the cultivar name 'Camp Bulewhit'. The new cultivar originated from a hybridization made in February 2000 in Andijk, The Netherlands. The female parent was 'CL-136-1', a proprietary (unpatented) bi-colored flowered *Campanula isophylla* plant, while the male parent was 'CL-34-1', a proprietary (unpatented) white-flowered *Campanula isophylla* plant. The seeds produced by the hybridization were sown in August 2000, and the resulting seedlings were selected in January 2002. A single plant selection was chosen for further evaluation and for asexual propagation in 2002.

The new cultivar was created in 2000 in Andijk, The Netherlands and has been asexually reproduced repeatedly by vegetative cuttings and tissue culture in Andijk, The Netherlands over a three-year period. 'Camp Bulewhit' has also been trialed at Hillscheid, Germany. The present invention has been found to retain its distinctive characteristics through successive asexual propagations.

Plant Breeder's Rights for this cultivar were applied for in Canada on Mar. 21, 2006 and with the European Union on Jan. 24, 2005.

SUMMARY OF THE INVENTION

The following are the most outstanding and distinguishing characteristics of this new cultivar when grown under normal horticultural practices in Andijk, The Netherlands and Hillscheid, Germany.

1. Large-sized, blue and white, star-shaped flowers;
2. An early and profuse flowering response;

3. Medium-green foliage with cordate leaves;
4. Moderately vigorous growth; and
5. A low, spreading and mounding, tight plant habit.

DESCRIPTION OF PHOTOGRAPHS

This new *campanula* plant is illustrated by the accompanying photographs which show overall plant habit including blooms, buds, and foliage of the plant; the colors shown are as true as can be reasonably obtained by conventional photographic procedures. The photographs are of 5-month-old plants grown in a greenhouse in Andijk, The Netherlands in May 2003.

DESCRIPTION OF THE NEW CULTIVAR

Figure 1:
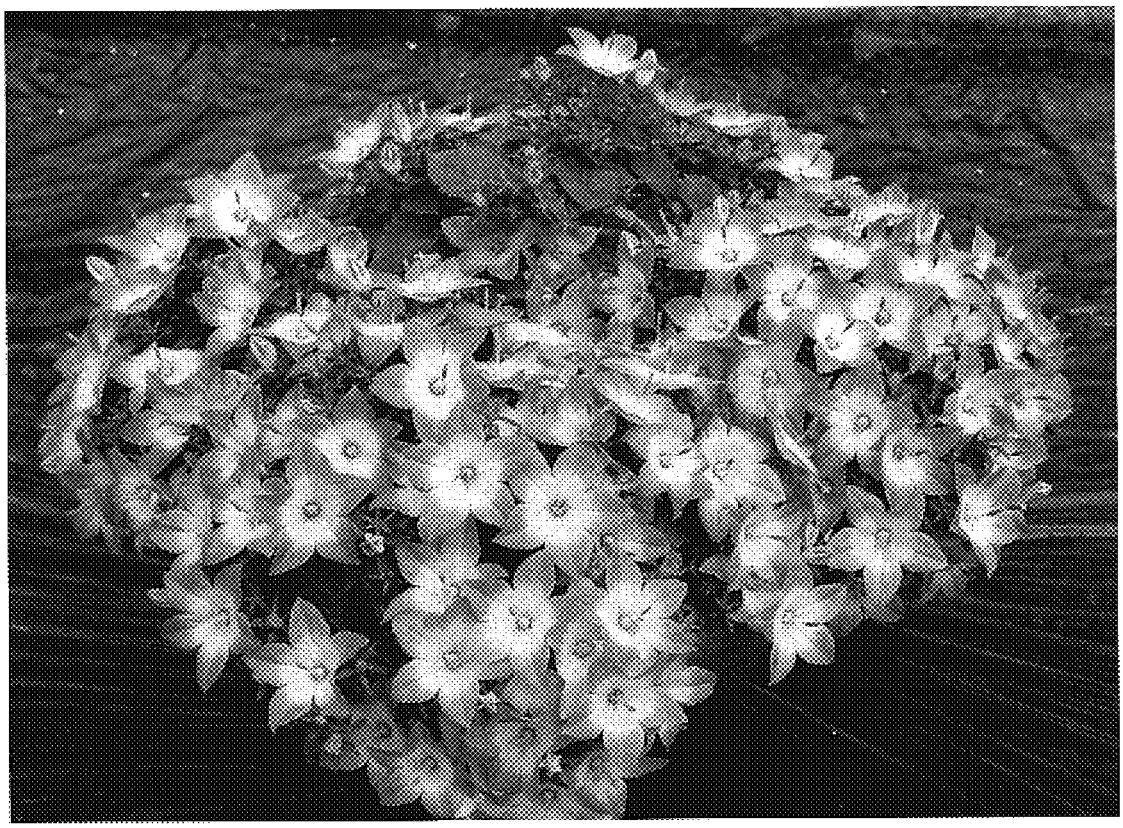
FIG. 1 shows the overall plant habit, including blooms, buds, foliage and plant habit.
Figure 2:
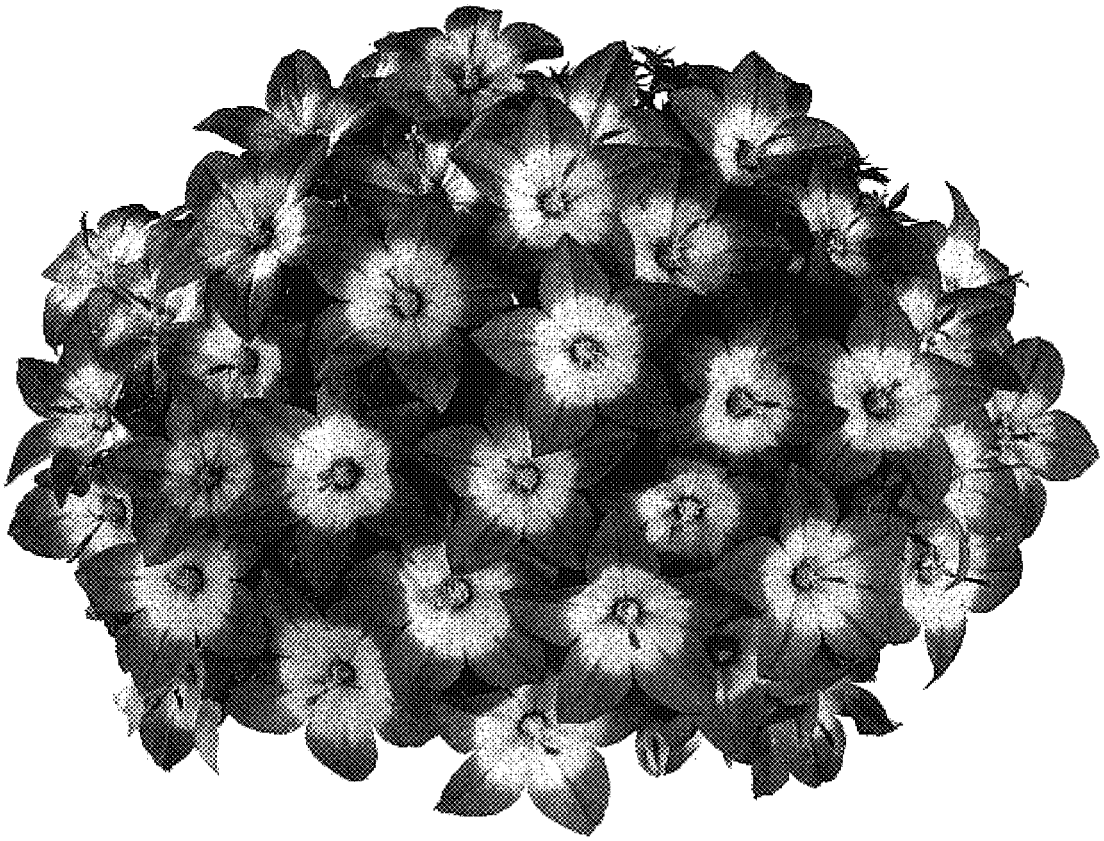
FIG. 2 shows a close-up of the mature inflorescences.

The following detailed description sets forth the distinctive characteristics of 'Camp Bulewhit'. The data which define these characteristics were collected from asexual reproductions carried out in Andijk, The Netherlands. The plant history was taken partly on 5-week old plants, still in a vegetative state and grown in Hillscheid, Germany in the spring of 2006. Rooted cuttings were planted in 10.5-cm pots and grown in a greenhouse. The plants were not pinched. Flower observations were made on 35-week-old plants in the fall of 2005. Color readings were taken under natural light. Color references are primarily to The R.H.S. Colour Chart of The Royal Horticultural Society of London (R.H.S.) (2001).

DETAILED BOTANICAL DESCRIPTION

Classification:
*Family.*—Campanulaceae.

*Botanical.*—*Campanula isophylla* Moretti.
*Common name.*—Italian Bellflower.

Parentage:
*Female parent.*—'CL-136-1', a proprietary bi-colored, blue and white flowered *Campanula isophylla* plant (unpatented).
*Male parent.*—'CL-34-1', a proprietary white-flowered *Campanula isophylla* plant (unpatented).

Growth:
*Form.*—Herbaceous perennial; for commercial purposes the variety can be cultivated as an annual.
*Habit.*—Initially upright, strong basal and secondary branching, later develops into a spreading and partly decumbent plant habit.
*Height* (*measured from the top of the soil*).—9.5 cm.
*Width* (*horizontal plant diameter*).—17 cm.
*Propagation.*—Terminal tips for cutting.
*Time to produce a finished flowering plant.*—11 to 13 weeks for a 10 cm to 12 cm pot.
*Outdoor plant performance.*—As flowering pot plants.
*Time to initiate and develop roots.*—25 days.
*Root description.*—Fibrous, fine and cream-white.

Stems:
*Number of basal branches.*—8 to 10.
*Length* (*measured from the base, not including the inflorescence*).—7 cm to 9 cm.
*Internode length.*—0.5 cm to 1.5 cm.
*Diameter* (*at midpoint*).—0.3 cm to 0.4 cm.
*Color.*—RHS 145A (light-green).
*Anthocyanin.*—None.
*Texture.*—Dense, fine pubescence.

Leaves:
*Arrangement.*—Alternate.
*Size.*—Length: 3.1 cm to 3.3 cm. Width: 3.7 cm to 4.2 cm.
*Shape.*—Cordate.
*Margin.*—Somewhat serrate or weakly dentate.
*Apex.*—Rounded to obtuse.
*Base.*—Cordate.
*Color.*—Immature leaves: Upper surface: RHS 138A. Lower surface: RHS 143B. Mature leaves: General: Deep green to medium green. Upper surface: RHS 137A. Lower surface: Between RHS 138A and RHS 138B.
*Texture.*—Leathery, with very short pubescence mostly along the margins and at the veins of the lower surface.
*Venation.*—Intermediate between palmate and pinnate, with the larger veins of the lower surface protruding.
*Venation color.*—RHS 144B, lower surface.
*Petioles.*—Length: 3.0 cm to 5.0 cm. Width: 0.2 cm. Color: RHS 143B (green). Texture: Robust with short hairs and hispid.

Flower bud:
*Shape.*—Narrow and oval (elongated) with deep furrows.
*Size.*—Length: 1.1 cm. Diameter: 0.6 cm.
*Color at tight bud.*—Mainly RHS 91B (pale-blue).

Inflorescence:
*Blooming habit.*—Continuous under long-day conditions.
*Inflorescence type.*—Terminal, bending and decumbent.
*Number of flowers per inflorescence.*—About 5 to 7 flowers and buds.
*Lastingness of individual blooms on the plant (at 18° C.).*—About 14 days.
*Fragrance.*—None.
*Length.*—3.5 cm to 5.0 cm.
*Diameter.*—3.5 cm to 4.5 cm.
*Peduncle.*—Length: 2.0 cm to 4.0 cm. Diameter: 0.2 cm. Color: RHS 145A (light-green). Texture: Sparse pubescence.
*Pedicels.*—Length: Up to 1.5 cm. Diameter: 0.2 cm. Color: RHS 143A (green). Anthocyanin: None. Texture: Sparse pubescence.

Flowers:
*Flower type.*—Campanulate.
*Corolla.*—Shape: Shallow cup-shaped; composed of 5 petals that are mainly fused and open outward. Size: Diameter: 3.7 cm. Depth: 0.7 cm. Color: General: Blue with white bases. Upper surface (petal lobes): RHS 91A. Upper surface (basal part): RHS 155D. Lower surface (petal lobes): RHS 91B. Lower surface (near base): RHS 91D.
*Petals.*—Shape: Roughly ovate. Size (from the opening): Length: 1.2 cm. Width: 1.1 cm. Quantity: 5. Apex: Broadly acute. Base: Fused. Margin: Entire. Texture: Smooth and glabrous.
*Calyx.*—Composed of 5 sepals fused at the base.
*Sepals.*—Number: 5. Color (both surfaces): RHS 143A (green). Length: 1.1 cm. Width: 0.4 cm to 0.5 cm. Shape: Narrowly ovate. Apex: Acute. Base: Fused. Margin: Entire. Texture: Covered with fine pubescence.

Reproductive organs:
*Stamens.*—Quantity: 5. Filament: Color: RHS 155D (white). Length: 0.2 cm. Diameter: 0.1 cm. Anther: Color: RHS 4C. Size: Length: 0.3 cm. Diameter: 0.1 cm or less. Pollen: Color: RHS 4D (pale-yellow). Amount: Moderate.
*Pistil.*—Quantity: 1. Length: 1.8 cm. Stigma: Color: RHS 150D (nearly-white). Shape: 3-lobed with brush-like-arranged hair below the stigma. Style: Color: RHS 91C (pale light-blue). Length: 1.3 cm.
*Ovary.*—Type: Intermediate. Shape: Ovate. Length: 0.4 cm. Diameter: 0.2 cm to 0.3 cm. Color: RHS 143A (green).

Fruit and seed set: None observed.
Disease and insect resistance: No special observations made.

COMPARISON WITH PARENTAL AND COMMERCIAL CULTIVARS

'Camp Bulewhit' differs from the female parent 'CL-136-1' (unpatented) in that 'Camp Bulewhit' has smaller, bi-colored flowers and a more evenly shaped plant habit than 'CL-136-1'. Additionally, 'Camp Bulewhit' has an earlier flowering response than 'CL-136-1'.

'Camp Bulewhit' differs from the male parent 'CL-34-1' (unpatented) in that 'Camp Bulewhit' has bi-colored blue and white flowers, while 'CL-34-1' has white flowers.

'Camp Bulewhit' differs from all known *Campanula* commercial varieties in that 'Camp Bulewhit' has bi-colored blue and white flowers, while all known *Campanula* commercial varieties have either uniformly white or blue colors.

I claim:

1. A new and distinct cultivar of *campanula* plant as shown and described herein.

* * * * *